United States Patent [19]

Ishiguro et al.

[11] Patent Number: 4,857,165
[45] Date of Patent: Aug. 15, 1989

[54] OXYGEN SENSING ELEMENT AND PROCESS OF MANUFACTURING THE SAME

[75] Inventors: Fujio Ishiguro; Takumi Narahara, both of Nagoya, Japan

[73] Assignee: NGK Insulators, Ltd., Japan

[21] Appl. No.: 154,030

[22] Filed: Feb. 9, 1988

[30] Foreign Application Priority Data

Feb. 16, 1987 [JP] Japan .................................. 62-32932

[51] Int. Cl.⁴ ........................................... G01N 27/58
[52] U.S. Cl. .................................. 204/424; 156/667; 427/125; 427/126.3; 501/103; 501/105
[58] Field of Search ............... 204/424, 421, 425, 426, 204/427, 428, 429, 422, 423, 1 S; 427/125, 126.3; 501/103, 105; 156/667

[56] References Cited

U.S. PATENT DOCUMENTS

| 4,183,798 | 1/1980 | Esper et al. ...................... 501/103 X |
| 4,318,770 | 3/1982 | Chakupurakal .................. 156/667 X |
| 4,328,294 | 5/1982 | Tanaka et al. .................... 204/424 X |
| 4,542,110 | 9/1985 | Nakada et al. ...................... 501/103 |

FOREIGN PATENT DOCUMENTS 67647  5/1980  Japan .

Primary Examiner—G. L. Kaplan
Attorney, Agent, or Firm—Arnold, White & Durkee

[57] ABSTRACT

An oxygen sensing element having an oxygen-ion conductive solid electrolyte body, a measuring and a reference electrode formed on the solid electrolyte body so as to communicate with a measurement and a reference gas, respectively. The solid electrolyte body is formed by firing an unfired body of an oxygen-ion conductive solid electrolyte material containing a sitnering aid. The firing temperature is selected within a range defined by a permissible lowest sintering point of the unfired formed body, and an upper limit which is 60° above the permissible lowest sintering point, whereby an amount of the sintering aid left on the surface of the first solid electrolyte body is smaller than that left within an interior structure of the solid electrolyte body, as viewed in a transverse cross sectional plane of the solid electrolyte body.

8 Claims, 2 Drawing Sheets

OXYGEN SENSING ELEMENT AND PROCESS OF MANUFACTURING THE SAME

BACKGROUND OF THE INVENTION

1. Field of the Invention

The present invention relates in general to an oxygen sensing element and a process of manufacturing the same, and more particularly to an oxygen sensing element for accurately determining an oxygen concentration in exhaust gases emitted in particular by internal combustion engines and boilers, wherein the sensing element assures a high operating response at a relatively low temperature.

2. Discussion of the Prior Art

It is known to use zirconia ceramics or other oxygen-ion conductive solid electrolyte materials, for determining an oxygen concentration in measurement gases such as exhaust gases produced by internal combustion engines of motor vehicles, or boilers, according to the principle of an oxygen concentration cell. Based on the determined oxygen concentration, an air/fuel ratio of an air-fuel mixture supplied to the engines or boilers is controlled to assure an optimum combustion or burning condition of the engines or boilers.

An oxygen sensor or detector for determining an oxygen concentration as indicated above includes a sensing element which uses a suitably shaped tubular or planar solid electrolyte body made of an oxygen-ion conductive solid electrolyte material. On the inner and outer surfaces of the solid electrolyte body, there are formed a pair of electrodes, respectively. One of the electrodes which is formed on the inner surface communicates with an ambient air or atmosphere so that it functions as a reference electrode exposed to the ambient air, which serves as a reference gas having a reference oxygen concentration. The other electrode formed on the outer surface of the solid electrolyte body communicates with exhaust gases so that it functions as a measuring electrode exposed to the exhaust gases, which serves as a measurement gas to be measured. The sensing element is adapted to detect an electromotive force which is induced between the reference and measuring electrodes, due to a difference in the oxygen concentration between the atmospheres to which the two electrodes are exposed. Thus, the oxygen concentration in the exhaust gases is determined.

It is known that a $\lambda$ (lambda) curve representing a relationship between the output of an oxygen sensor of the type discussed above and the air/fuel ratio (A/F ratio) of an air-fuel mixture supplied to a gasoline engine, for example, ideally exhibits a sudden drop in the sensor output, at the stoichiometric A/F ratio, i.e., $A/F = 14.7$ for a gasoline engine, as indicated in FIG. 1. This sudden change of the sensor output at the stoichiometric A/F ratio of 14.7 is utilized to control the A/F ratio of the air-fuel mixture.

In the known oxygen sensor, however, the A/F ratio at which the sensor output suddenly changes tends to be deviated or shifted away from the stoichiometric point on the side of higher A/F ratio values (to the right as viewed in the graph of FIG. 1) particularly when the temperature of the exhaust gases is relatively low, whereby the air/fuel ratio of the air-fuel mixture cannot be maintained at the stoichiometric point. This tendency has an adverse effect, from the standpoint of purification of the exhaust gases which result from the controlled air-fuel mixture.

To solve the above problem encountered when the temperature of the exhaust gases is low, there have been proposed various heater-built-in oxygen sensors which employ a heater for heating the oxygen sensing element, so that the sensing element is maintained at an optimum operating temperature even when the temperature of the exhaust gases is low. Certainly, such heater-built-in sensors are complicated in construction due to the incorporation of the heater within the sensor body, and are consequently less economical to manufacture.

SUMMARY OF THE INVENTION

The present invention was developed in light of the above problem experienced in the prior art. It is accordingly a first object of the present invention to provide an inexpensive oxygen sensor which exhibits an ideal relationship between its output and the A/F ratio of an air-fuel mixture (ideal lambda curve), even when the temperature of the measurement gas is relatively low.

A second object of the invention is to provide a process suitable for manufacturing such an oxygen sensor.

The first object may be achieved according to the principle of one aspect of the present invention, which provides an oxygen sensing element having a solid electrolyte body made of an oxygen-ion conductive solid electrolyte material, and a measuring electrode and a reference electrode formed on the solid electrolyte body, said measuring and reference electrodes respectively communicating with a measurement gas, and a reference gas having a predetermined oxygen concentration, so that an electromotive force is induced between the measuring and reference electrodes, based on a difference in oxygen concentration between the measurement gas and the reference gas, wherein the improvement comprises a sintering aid which is left on the surface of the solid electrolyte body in an amount smaller than that left within an interior of the solid electrolyte body, as viewed in a cross sectional plane of the solid electrolyte body.

The second object of the invention may be attained according to another aspect of the present invention, which provides a process of manufacturing an oxygen sensing element having a solid electrolyte body made of an solid electrolyte body, said measuring and reference electrodes respectively communicating with a measurement gas, and a reference gas having a predetermined oxygen concentration, so that an electromotive force is induced between the measuring and reference electrodes, based on a difference in oxygen concentration between the measurement gas and the reference gas, the instant method comprising the steps of preparing an unfired formed body of the solid electrolyte body, and firing the unfired formed body into the solid electrolyte body, at a temperature within a range which is defined by a permissible lowest sintering point and a point which is 60° C. above the permissible lowest sintering point. Preferably, the instant process may further comprise a step of chemically treating the fired surface of the solid electrolyte body, and thereby reducing or removing a sintering aid on the chemically treated surface.

According to the present invention described above, the amount of the sintering aid left on the surface of the fired solid electrolyte body is smaller than that left within the interior of the solid electrolyte body. This enables the oxygen sensing element to exhibit an ideal output-A/F ratio curve representing a relationship between its output and the A/F ratio of an air-fuel mixture, even when the temperature of the measurement gas produced as a result of combustion of the air-fuel mixture is relatively low. Described more specifically, it is presumed that the reduction or removal of the sintering aid, such as $SiO_2$ in particular, from the oxygen-ion conductive solid electrolyte material contributes to minimizing an adverse influence of the sintering aid on a material of the electrodes such as platinum, thereby improving the function of the electrodes as a catalyst, and thus contributes to enhancing the output characteristic of the sensing element with respect to the A/F ratio of the air-fuel mixture. The other presumed contributory factors include the prevention of adhesion of the solid electrolyte body and the electrodes by a glass layer which may be easily formed on the surface of the solid electrolyte body, by means of the sintering aid otherwise existing in a comparatively large amount on the solid electrolyte surface.

According to the manufacturing process of the present invention, the unfired formed body is fired into the solid electrolyte body, at a temperature as low as possible. This low firing temperature is considered effective to reduce the diffusion of the sintering aid from the interior structure of the solid electrolyte body up to the surface. The sintering aid which may still exist in a small amount on the solid electrolyte surface may be relatively easily removed by a subsequent chemical treatment, leading to a further improvement of the output characteristic of the sensor. Moreover, the reduced amount of the sintering aid existing on the solid electrolyte surface requires the chemical surface treatment to be performed under a relatively mild condition, whereby the chemical treatment does not cause deterioration of the oxygen-ion conductive solid electrolyte material or reduction in the strength of the solid electrolyte body. For this reason, the combination of the relatively low firing temperature and the chemical surface treatment is particularly advantageous to produce a reliable oxygen sensing element according to the present invention.

In the instant process, the composition and content of the sintering aid can be freely selected, so as to minimize an adverse effect on the sensing capability of the sensing element. In other words, the sintering temperature of the solid electrolyte can be readily determined or adjusted. Furthermore, the instant process eliminates the need of strictly controlling the sinterability of the solid electrolyte material such as zirconia, by limiting the grain size of the solid electrolyte material to within a suitable range. In this respect, the process of the invention permits comparatively easy manufacture of the sensing element.

BRIEF DESCRIPTION OF THE DRAWINGS

The above and optional objects, features and advantages of the present invention will become more apparent by reading the following detailed description of the invention, when considered in connection with the accompanying drawings, in which.

DETAILED DESCRIPTION OF THE INVENTION

Figure 1:
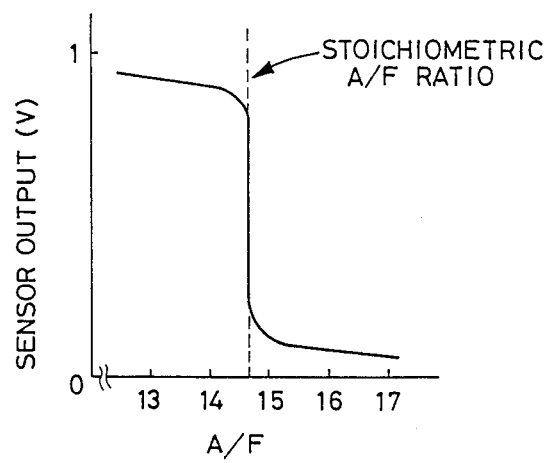
FIG. 1 is a graph showing a relationship between an output of an oxygen sensor, and an air/fuel ratio of an air-fuel mixture.

The oxygen-ion conductive solid electrolyte for the solid electrolyte body (as a main body of the oxygen sensing element) can be selected from among various known solid electrolyte materials, but is preferably formed of a fully or partially stabilized zirconia which includes a suitable stabilizing agent such as yttria ($Y_2O_3$), calcia (CaO), magnesia (MgO) or ytterbia ($Yb_2O_3$) Further, the solid electrolyte is mixed with a suitable sintering aid, for example, clay such as kaoline, or $SiO_2$, $Al_2O_3$ or, $Fe_2O_3$ The selected solid electrolyte material containing a sintering aid is formed into an unfired body having a desired shape, by a known technique such as a press molding process by using a rubber press, for example. As described below, the thus prepared unfired formed body gives, by firing thereof, the fired solid electrolyte body having a tubular or other desired configuration, which constitutes a main body of the oxygen sensing element.

Then, the unfired formed body may be calcined as needed, at a temperature lower than a firing temperature. The calcined or non-calcined formed body is fired in an ordinary known manner, but at a firing temperature which falls within a specific range determined according to the principle of the invention. That is, the firing temperature range is defined by a lower limit equal to a permissible lowest sintering point at which the solid electrolyte material can be sintered, and an upper limit which is 60° C. above the permissible lowest sintering point. The firing operation within the above temperature range makes it possible to effectively prevent the sintering aid from diffusing from the interior of the solid electrolyte body up to its surface. The term "permissible sintering point" used herein should be interpreted to mean a firing temperature above which the open porosity of a test piece (tablet) fired for three hours is smaller than 0.10%.

It is preferred that the thus fired solid electrolyte body of the sensing element is chemically treated to reduce or remove the sintering aid such as $SiO_2$ that is left on the surface of the body. This chemical treatment permits further or more effective reduction in the amount of the sintering aid left on the surface of the solid electrolyte body, as compared with the amount of the same left within the interior structure of the body.

The chemical treatment to reduce or eliminate the remaining sintering aid on the solid electrolyte surface may be conducted effectively by utilizing an aqueous solution of acids such as HF and HCl, or alternatively an aqueous solution of alkali such as NaOH. The conditions of the chemical treatment, such as treatment temperature and time, are suitably determined, depending upon the amount of the sintering aid that is left on the surface of the solid electrolyte body.

The amounts or distribution of the sintering aid left on the surface and within the interior of the thus prepared oxygen-ion conductive solid electrolyte body of the oxygen sensing element can be detected by cutting the solid electrolyte body in a desired plane passing through the solid electrolyte body, and observing the cut surface and/or the outer surface of the body, by surface analysis using a device such as an X-ray Photoelectron Spectroscopy Analyzer (XPS) or an Electron Probe Micro Analyzer (EPMA), for instance. In the solid electrolyte body prepared as described above, the analysis by such an analyzing instrument reveals that the amount of the sintering aid existing on the surface of the body (i.e., adjacent to the edges of the cut surface of the solid electrolyte body) is smaller, than that within the interior structure of the body, for example, at a depth 100 microns inward of the surface. This distribution of the sintering aid residue enables the oxygen sensing element to exhibit an ideal A/F ratio-output characteristic curve, as shown in FIG. 1, that assures accurate determination of the oxygen concentration of the exhaust gases, and consequently accurate determination of the A/F ratio of an air-fuel mixture from which the exhaust gases are produced.

On the surface of the solid electrolyte body at which the residue of the sintering aid is reduced as described above, there are formed at least a measuring electrode and a reference electrode, which are exposed to the measurement gas (exhaust gases) and the reference gas, respectively. These electrodes are thin layers formed of an electrically conductive material which consists of, or includes as a major component, a metal of the platinum group, such as platinum, ruthenium, osmium, iridium, rhodium and palladium. The electrodes are formed by one of various known methods, for example: plating; sputtering; thermal decomposition of salt of selected metal; or firing of a metal paste applied to the solid electrolyte body.

After the measuring electrode is formed on the surface of the solid electrolyte body as described above, the measuring electrode may be covered as needed, by a porous ceramic protective overcoat having a suitable thickness, in order to increase the durability of the measuring electrode. This ceramic protective overcoat can be formed by various known methods, commonly by applying a selected ceramic material over the measuring electrode, by a plasma or flame spraying method, preferably by the plasma spraying method. In the preferred plasma spraying method, the selected ceramic material, usually, spinel ($Al_2O_3 \cdot MgO$) is sprayed by a plasma flame of $Ar/N_2$ or $N_2/H_2$ gas, so as to cover the measuring electrode.

The oxygen sensing element thus manufactured is capable of providing an ideal λ curve, that is, an output characteristic wherein the output level suddenly drops substantially at the stoichiometric A/F ratio (as indicated in FIG. 1), even when the operating temperature is relatively low. Therefore, an oxygen sensor using the instant oxygen sensing element is capable of accurately determining the A/F ratio of the air-fuel mixture, by detecting its output level.

EXAMPLES

To further clarify the concept of the present invention, some typical examples of the invention will be illustrated. However, it is to be understood that the invention is by no means limited to the precise details of the illustrated examples.

It is further to be understood that the present invention may be embodied with various changes, modifications and improvements, which may occur to those skilled in the art, without departing from the spirit and scope of the present invention.

Initially, 100 parts by weight of a mixture consisting of 94 mole % of zirconia and 6 mole % of yttria was mixed with each of three sintering aid compositions A, B and C. As indicated in Table 1, the sintering aid composition A consists of 1.0 parts by weight of $SiO_2$ and 1.0 part by weight of $Al_2O_3$, and the sintering aid composition B consists of 1.0 parts by weight of $SiO_2$, 1.2 parts by weight of $Al_2O_3$ and 0.5 parts by weight of $TiO_2$ Further, the composition C consists of 0.8 parts by weight of $SiO_2$, 1.2 parts by weight of $Al_2O_3$, 0.5 part by weight of $TiO_2$ and 0.5 parts by weight of $Fe_2O_3$ The mass of each sintering aid composition was evenly mixed and crushed, with $ZrO_2$ balls, for 6 hours in a ball mill. The crushed mass was calcined in air for 3 hours at 1000° C. Then, calcined mass was wet-crushed for 20 hours in the ball mill, whereby a slurry was obtained. To the obtained slurry was added 1% by weight (with respect to a solid content of the slurry) of polyvinyl alcohol as a binder. Then, the slurry was processed by a spray drier so as to prepare a solid electrolyte material in the form of granules whose grain size is about 50 microns. Thus, the three different granular solid electrolyte materials were prepared.

By using the individual granular solid electrolyte materials, there were formed respective specimens in the form of unfired tablets whose density at their surface is equal to that of an unfired formed body which gives a solid electrolyte body of an actually produced sensing element. The permissible lowest sintering temperature of each specimen was experimentally determined. The determined lowest sintering temperatures are also indicated in Table 1. In determining the lowest sintering temperatures, the tablets of each specimen were fired for 3 hours, at respective temperatures different from each other by 20° C. The open porosity, i.e., a ratio of open pores of each fired tablet was measured. The lowest firing temperature which enabled the corresponding fired tablet to have the open porosity lower than 0.10%, was determined to be the permissible lowest sintering temperature for the specimen involved.

In the meantime, ten test pieces of an unfired tubular body for a tubular oxygen sensing element having an ordinary known configuration were prepared from each of the three different granular solid electrolyte materials. The prepared ten pieces of each material were fired at respective temperatures which include the permissible lowest sintering temperature determined as described above. These temperatures are different from each other in increments of 20° C. Some of the thus fired tubular solid electrolyte bodies were chemically treated under the conditions specified in Table 1, and platinum electrodes were formed by an ordinary plating method, on the chemically treated surface of each solid electrolyte body. Thereafter, a protective overcoat of spinel having a thickness of about 100 microns was formed on the measuring electrode, by a plasma spraying method.

On the rest of the fired tubular solid electrolyte bodies, there were formed the electrodes and the protective overcoats, without prior chemical treatment of the solid electrolyte surface.

Each of the thus prepared oxygen sensing elements was incorporated into a metallic housing, as in a known oxygen sensor. The sensing elements were tested for operating characteristics, in the following manner.

Each sensing element was installed such that the detecting portion was exposed to exhaust gases in an exhaust pipe of a 4-cylinder gasoline engine (having a 1.5 liter displacement). The temperature of the exhaust gases at the detecting portion of the sensing element was maintained within a range of 280°–300° C. In this condition, the output of the sensing element was measured by changing the A/F ratio of the air-fuel mixture supplied to the engine. The A/F ratios obtained at the sensor output of 0.3V were indicated in Table 1, and FIGS. 2 and 3.

Figure 2:
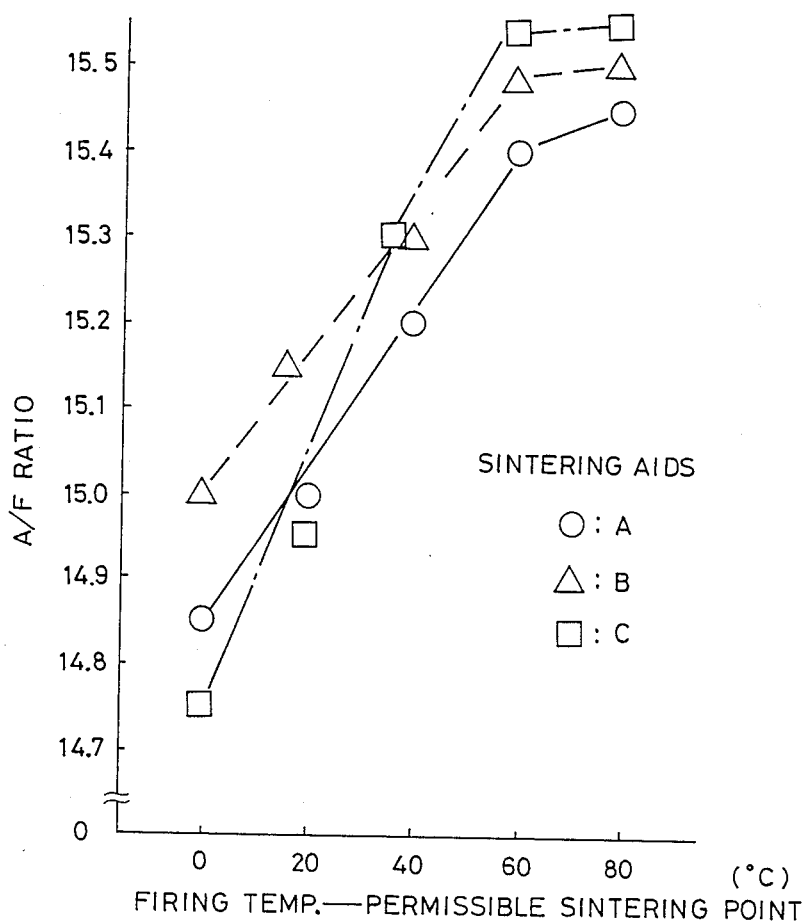
FIG. 2 is a graph relating to various specimens of oxygen sensing elements, showing relationships between the air/fuel ratio at the sensor output of 0.3 v, and a difference between an actual firing temperature and a permissible lowest sintering temperature of the solid electrolyte of the sensing element, where the solid electrolyte body is not chemically treated.
Figure 3:
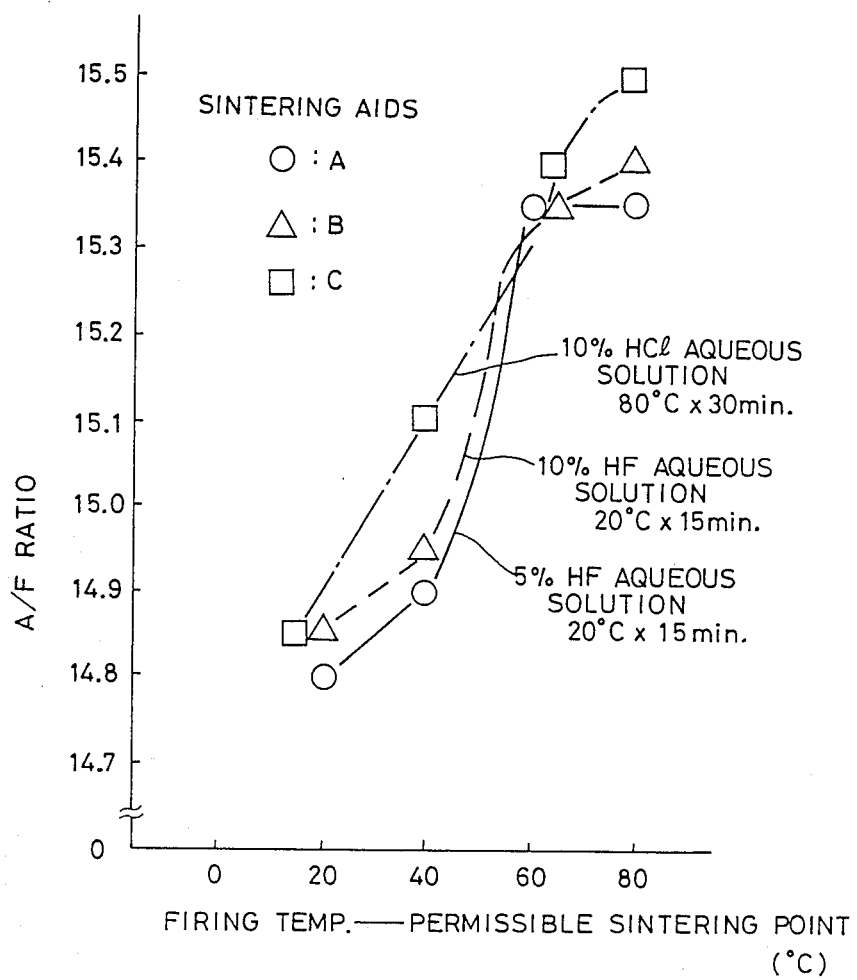
FIG. 3 is a graph showing the same relationships as shown in FIG. 2, where the solid electrolyte body is chemically treated.

FIGS. 2 and 3 show the obtained relationships between the A/F ratio indicated above, and a difference between the actually used firing temperature and the determined permissible lowest sintering temperature, with respect to the sensing elements prepared from the different solid electrolyte materials which contain the different sintering aid compositions A, B and C. The graph of FIG. 2 represents the relationships of the sensing elements whose solid electrolyte bodies were not chemically treated, while the graph of FIG. 3 represents those of the sensing elements whose solid electrolyte bodies were chemically treated before the electrodes were formed thereon.

It follows from Table 1 and FIGS. 2 and 3 that the A/F ratio obtained at the sensor output of 0.3V approaches the stochiometric point (14.7) as the firing temperature of the solid electrolyte bodies approaches the permissible lowest sintering temperatures of the solid electrolyte materials used. It is further apparent that the A/F ratios obtained on the sensing elements prepared from the chemically treated solid electrolyte bodies are nearer to the stoichiometric point, than those obtained on the sensing elements prepared from the solid electrolyte bodies which were not chemically treated before the electrodes were formed thereon.

Some of the prepared oxygen sensing elements were cut in a transverse cross sectional plane, to make a qualitative (semi-quantitative) analysis of the distribution of Si (used as a component of the sintering aid composition) in the transverse direction of the sensing elements. This analysis was conducted on the cut surface by using an Electron Probe Micro Analyzer. The analysis confirmed that a trace amount of Si was left on or right below the surface (substantially perpendicular to the cut surface) of the sensing elements of Example Nos. 1, 4, 7 and 8 (Table 1), but this amount was significantly smaller that the amount left in the transversely interior structure of the sensing elements. However, the analysis revealed a considerably large amount of Si left on the surface of the sensing element of Example No. 10 prepared as a comparative example. The analysis showed no amount of Si left on the surface of the sensing elements of Example Nos. 2, 3, 5, 6 and 9.

TABLE 1

| No. | Sintering Aid | Sintering Temp. | Chemical Treatment | A/F ratio |
|---|---|---|---|---|
| 1 | A = 1.0 wt. % $SiO_2$ | 1480° C. | None | 14.85 |
| 2 | 1.0 wt. % $Al_2O_3$ | 1500° C. | 5% HF aqueous solution | 14.8 |
| 3 | Lowest Sintering Temp. = 1480° C. | 1520° C. | 20° C. × 15 minutes | 14.9 |
| 4 | B = 1.0 wt. % $SiO_2$ | 1440° C. | None | 15.0 |
| 5 | 1.2 wt. % $Al_2O_3$ | 1460° C. |  | 14.85 |
|  | 0.5 wt. % $TiO_2$ |  | 10% HF aqueous solution |  |
| 6 | Lowest Sintering Temp. = 1440° C. | 1480° C. | 20°C. × 15 minutes | 14.95 |
| 7 | C = 0.8 wt. % $SiO_2$ | 1400° C. | 10% HCl aqueous solution | 14.75 |
|  | 1.2 wt. % $Al_2O_3$ |  |  |  |
| 8 | 0.5 wt. % $TiO_2$ | 1420° C. | 80° C. × 30 minutes | 14.87 |
|  | 0.5 wt. % $Fe_2O_3$ |  |  |  |
| 9 | Lowest Sintering Temp. = 1400° C. | 1440° C. | 10% HF aqueous solution 20° C. × 15 minutes | 14.7 |
| 10 | A (See above.) | 1540° C. | None | 15.4 |

What is claimed is:

1. A process of manufacturing an oxygen sensing element having a solid electrolyte body made of an oxygen-ion conductive solid electrolyte material, and a measuring electrode and a reference electrode formed on the solid electrolyte body in communication with a measurement gas and a reference gas having a predetermined oxygen concentration, respectively, such that an electromotive force is induced between the measuring and reference electrodes based on a difference in oxygen concentration between the measurement gas and the reference gas, said method comprising the steps of:
   preparing an unfired formed body of said solid electrolyte body using said oxygen-ion conductive solid electrolyte material mixed with a sintering aid;
   firing said unfired formed body into said solid electrolyte body at a temperature within a range which is defined by a permissible lowest sintering point of said unfired formed body and a point which is 60° C. above said permissible lowest sintering point; and
   chemically treating the fired surface of said solid electrolyte body under a condition whereby the oxygen-ion conductive solid electrolyte material is not deteriorated and the strength of the solid electrolyte body is not reduced;
   said chemical treatment being carried out to such an extent that an amount of the sintering aid left on the surface of said solid electrolyte body is smaller than that left within an interior structure of the solid electrolyte body, as viewed in a transverse cross sectional plane of the solid electrolyte body.

2. A process according to claim 1, wherein said step of chemically treating the fired surface of said solid electrolyte body comprises exposing said fired surface to a solution containing no more than 10% of acid.

3. A process according to claim 1, wherein said solid electrolyte material consists of zirconia fully or partially stabilized by a stabilizing agent.

4. An oxygen sensing element having an oxygen-ion conductive solid electrolyte body, a measuring electrode formed on the solid electrolyte body in communication with a measurement gas, and a reference electrode formed on the solid electrolyte body in communication with a reference gas having a predetermined oxygen concentration, such that an electromotive force is induced between the measuring and reference electrodes based on a difference in oxygen concentration between the measurement gas and the reference gas;

wherein said oxygen-ion conductive solid electrolyte body is formed by a process comprising:

preparing an unfired formed body of the solid electrolyte body from an oxygen-ion conductive solid electrolyte material mixed with a sintering aid;

firing said unfired formed body into said solid electrolyte body at a firing temperature selected within a range which is defined by a lower limit equal to a permissible lowest sintering point of said unfired formed body and an upper limit which is 60° C. above the permissible lowest sintering point; and chemically treating the fired surface of said solid electrolyte body under a condition whereby the oxygen-ion conductive solid electrolyte material is not deteriorated and the strength of the solid electrolyte body is not reduced;

said chemical treatment being carried out to such an extent that an amount of the sintering aid left on the surface of said solid electrolyte body is smaller than that left within an interior structure of the solid electrolyte body, as viewed in a transverse cross sectional plane of the solid electrolyte body.

5. An oxygen sensing element according to claim 4, wherein said solid electrolyte material consists of ziconium fully or partially stabilized by a stabilizing agent.

6. An oxygen sensing element according to claim 4, wherein said sintering aid comprises $SiO_2$.

7. An oxygen sensing element according to claim 4, wherein said step of chemically treating the fired surface of said solid electrolyte body comprises exposing said fired surface to a solution containing no more than 10% of acid.

8. An oxygen sensing element according to claim 4, wherein said step of chemically treating the fired surface of said solid electrolyte body is performed at a temperature of not greater than 80° C.

* * * * *